(12) United States Patent
Park (10) Patent No.: US 11,147,555 B2
(45) Date of Patent: Oct. 19, 2021

(54) SURGICAL BRACE DEVICE FOR STAPLED TISSUE

(71) Applicant: Chul Hi Park, Seoul (KR)

(72) Inventor: Chul Hi Park, Seoul (KR)

( * ) Notice: Subject to any disclaimer, the term of this patent is extended or adjusted under 35 U.S.C. 154(b) by 169 days.

(21) Appl. No.: 16/679,205

(22) Filed: Nov. 10, 2019

(65) Prior Publication Data

US 2020/0069310 A1 Mar. 5, 2020

Related U.S. Application Data

(63) Continuation of application No. 15/642,333, filed on Jul. 6, 2017, now Pat. No. 10,512,464.

(60) Provisional application No. 62/360,912, filed on Jul. 11, 2016.

(51) Int. Cl.
*A61B 17/072* (2006.01)
*A61B 17/122* (2006.01)
*A61B 17/00* (2006.01)

(52) U.S. Cl.
CPC .. *A61B 17/07292* (2013.01); *A61B 17/07207* (2013.01); *A61B 17/1227* (2013.01); *A61B 2017/00004* (2013.01); *A61B 2017/07285* (2013.01)

(58) Field of Classification Search
CPC .......... A61B 17/1227; A61B 17/07207; A61B 17/07292; A61B 17/068
See application file for complete search history.

(56) References Cited

U.S. PATENT DOCUMENTS

| | | | | |
|---|---|---|---|---|
| 5,620,452 A | * | 4/1997 | Yoon | A61B 17/0643 606/151 |
| 5,833,695 A | * | 11/1998 | Yoon | A61B 17/07207 606/139 |
| 8,920,305 B2 | * | 12/2014 | Jacobs | A61B 17/122 600/37 |
| 8,998,935 B2 | * | 4/2015 | Hart | A61B 17/105 606/157 |
| 10,512,464 B2 | * | 12/2019 | Park | A61B 17/07207 |
| 2013/0068821 A1 | * | 3/2013 | Huitema | A61B 17/07292 227/180.1 |

* cited by examiner

*Primary Examiner* — Nathaniel C Chukwurah (57) ABSTRACT

A surgical brace device for use in a surgical procedure including surgical stapling operations on bodily organ to protect the stapled tissue against damaging effects of physiological motion of the organ is disclosed herein. The surgical brace device comprises a pair of splint members of a predetermined rigidity profile, configured to be disposed on either side of the stapled tissue and dimensioned to span at least a portion of the width thereof; a strut member fixedly joined with the pair of splint members at one ends thereof; and a tie member configured to traverse the tissue of the organ disposed at a predetermined distance from the plurality of strut members to interconnect the pair of splint members and anchor the surgical brace device thereto.

3 Claims, 7 Drawing Sheets

SURGICAL BRACE DEVICE FOR STAPLED TISSUE

CROSS REFERENCE TO RELATED APPLICATIONS

The present application is a Continuation application which claims the benefit of and priority to U.S. patent application Ser. No. 15/642,333, filed Jul. 6, 2017, which claims the benefit of and priority to U.S. Provisional Patent Application No. 62/360,912, filed on Jul. 11, 2016, the entire content of which is incorporated by reference.

TECHNICAL FIELD

The present invention relates to a medical device for use in surgical procedures. More particularly, the present invention relates to a surgical device for protecting a surgically stapled tissue of a bodily organ from failure caused by the technical limitations of the present surgical stapling technology and damaging effects of organ motion.

BACKGROUND OF THE INVENTION

The utilization of mechanical tissue fastening instruments, notably, surgical staplers and endo-cutters have been increasing steadily in recent years as a substitute for suturing in joining a tissue, joining and cutting a tissue simultaneously and performing anastomosis of tubular organs belonging to the digestive system in a number of surgical disciplines. Over the years these instruments have proven to provide significant clinical benefits of improved patient outcome in addition to procedural benefits of reduced procedure time and simplified surgical tasks when compared to laborious and time consuming suturing, and related cost savings. In certain types of surgical procedures use of surgical staplers/endo-cutters has become the preferred method of joining a tissue including the bariatric, thoracic and colorectal surgeries.

In order to address the specific needs of various surgical procedures, surgical stapler instruments have been developed and are disclosed in, for example, U.S. Pat. No. 5,040,715 (Green, et. al.); U.S. Pat. No. 5,307,976 (Olson, et. al.); U.S. Pat. No. 5,312,023 (Green, et. al.); U.S. Pat. No. 5,318,221 (Green, et. al.); U.S. Pat. No. 5,326,013 (Green, et. al.); and U.S. Pat. No. 5,332,142 (Robinson, et. al) which are each herein incorporated by reference. Intra-luminal or circular stapler instruments have also been developed for use in an anastomosis procedure as disclosed, for example, in U.S. Pat. Nos. 5,104,025 and 5,309,927 which are each herein incorporated by reference.

Known surgical stapler instruments include an end effector that simultaneously makes a longitudinal incision in tissue and applies lines of staples on opposing sides of the incision. The end effector includes a pair of opposed jaw members, rotatably engaged with each other about a pivot at the proximal ends of the jaw members, which, if the instrument is intended for endoscopic or laparoscopic applications, are capable of passing through a cannula passageway or a trocar port. One of the jaw members receives a staple cartridge having at least two laterally spaced rows of staples. The other jaw member defines an anvil having staple-forming pockets aligned with the rows of staples in the staple cartridge. The instrument commonly includes a plurality of reciprocating wedges which, when driven distally, pass through openings in the staple cartridge and engage drivers supporting the staples to effect the firing of the staples toward the anvil. When a surgical stapler instrument are used on an organ, such as the lung, stomach and intestine, integrity of the deployed staple line is usually checked with a static pressure leak test immediately following the stapling operation whereby the lumen of the stapled tubular organ is inflated with air to a predetermined pressure to look for visible signs of leak, e.g., bubbles from the staple line submerged in saline water.

The static pressure leak test may provide convenient indications for obvious defects in the line of stapled tissue, for example, due to malformed staples or damage to stapled tissue as a result of over-compression of tissue, at the time of stapling operation but not viability of staple line over a long term. Reports of staple line failures are not uncommon and symptoms thereof may present soon after a surgical procedure, for example, air leaks immediately following a high percentage of lung volume reduction surgeries, or several weeks after discharge of patient, for example, delayed complications following sleeve gastrectomy or colectomy. Failure of staple line may result in luminal contents, air in the lung and liquid content in the digestive tract, leaking into bodily cavity potentially causing morbidity prolonging recovery or even mortality. Precise causes of staple line failures have not been thoroughly studied and understood but the factors, associated with technical aspects of the present state of art of surgical stapling, including weakening of stapled tissue due to over-compression, under-compression of tissue, malformation of staples and weakening of stapled tissue at the intersection of two staple lines, etc. are believed to strongly influence quality and clinical outcome of a surgical stapling operation. In some cases a physician is known to "over-sow" or apply stitches across a line of stapled tissue to reinforce the staple line and to guard against potential failure of the staple line but there have been reports of the suture causing tearing of tissue it is meant to protect. Therefore, significant need exists for means to guard against potential staple line failure arising from known technical limitations inherent to the present state of the art of the surgical stapling technology.

It has been proven through clinical experiences that a static pressure leak test immediately following a surgical stapling operation on an organ having a lumen, such as the lung, stomach and colon, does not provide any reliable indicator as to long term viability of a staple line. These organs exert dynamic load significantly varying in magnitude and frequency as well as temporal pattern on a line of stapled tissue thereon as they undergo cyclic, periodic or irregular physiological motions, e.g., breathing (and occasional coughing) in case of the lung and peristaltic motion (and bolus load in the initial meal intake) in case of the digestive tracts. Partly due to complex nature of the physiological organ motions there are no practical ways to study and quantify, on empirical and/or theoretical basis, stresses on the stapled tissue resulting therefrom and their impacts, in short and long term, on the quality and clinical outcome of a stapling operation on these organs. However, those of skill in the art could appreciate qualitatively the potentially damaging effects of various physiological organ motions by examining the following analysis.

The wall tissue of the lung undergoes cyclic distensions during normal breathing cycles, which could exert dynamic tensile stress, on a stapled tissue thereon, of sizable magnitude due to shear size of the lung despite of relatively low pressure in the lumen thereof averaging at a small fraction of the ambient atmospheric pressure. The total number of breathing cycles and in turn, the cyclic dynamic tensile stress loads on the stapled tissue during average length of healing period of the stapled tissue, a few weeks, is in the millions. In addition, during occasional coughing the lumen pressure may reach a considerable fraction of the ambient atmospheric pressure and the peak tensile stress on the stapled tissue resulting from a coughing could be very high again due to a large size of the lung. The cumulative damaging effects of a series of coughing or in the worst case a single coughing may well prove to be catastrophic to the integrity of the stapled tissue already weakened by the staples penetrating there-through. The fact that the luminal content contained by the lung is air, being more lubricious and capable of slipping even through small opening than a liquid, under pressure likely exacerbates the problem evidenced by not so uncommon cases of air leaks following the lung surgeries involving stapling operations.

The wall tissue of the stomach undergoes somewhat periodic distention during peristaltic digestion motion following intake of meal. Although occurrence is less frequent than or as cyclic as breathing, each period of distention during peristaltic motion of the stomach (incidentally that of the colon) and resultant dynamic stress load on a stapled tissue on the organ may last significantly longer than a breathing cycle and its temporal pattern and average/peak magnitude may vary more significantly, particularly in the initial phase of a meal due to the bolus load, than those resulting from normal breathing, if not, coughing. Non-uniformity in the thickness of the stomach wall tissue may lead to uneven distribution over the line of stapled tissue of the dynamic tensile stress load being concentrated more on the thinner portion thereof, which tends to be weaker than the rest as well. Symptoms of staple line failures after the stomach and colon surgeries, such as a sleeve gastrectomy and colectomy, have been observed to show in wide range of timeframe anywhere between during hospital stay and several weeks after patient discharge. A plausible explanation for such phenomena could be presence of slowly progressing underlying causes of the staple line failures including ischemia of a portion of stapled tissue due to over-compression during a stapling operation and mechanical failure due to cumulative tensile stress loads brought on by the organ motion. The present surgical stapler technology has been developed or since evolved without much consideration of the potentially damaging effects of the organ motions on the clinical outcome of surgery involving stapling operation. Neither has ever been any secondary product introduced into the surgical stapler instrument market, which aims specifically to addresses such issues.

Therefore, it is an object of this invention to provide a surgical device to reduce probability of staple line failures due to known technical limitations of the present state of the art of the surgical stapling technology and damaging effects of organ motion.

BRIEF SUMMARY OF THE INVENTION

The present invention relates to a medical device for use in surgical procedures. More particularly, the present invention relates to a surgical device for protecting a surgically stapled tissue of a bodily organ from failure caused by the technical limitations of the present surgical stapling technology and damaging effects of organ motion.

In order to achieve the objects of the present invention, there is provided a surgical brace device for deployment across a line of surgically stapled tissue of a bodily organ. In an aspect of the present invention the surgical brace device is configured to create a redundant line of joined tissue adjacent to the line of stapled tissue at least partially continuously along the length thereof or in selected regions thereof with suspected weakness, which reduces probability of failure of the line of stapled tissue in the event where a portion thereof fails to properly heal to form a seal. In an alternate aspect, the surgical brace device is configured to prevent the line of stapled tissue from being pulled apart due to dynamic tensile stress load present on tissue of the organ during physiological motion thereof by absorbing a substantial fraction of energy associated with the tensile stress load. In another alternate aspect, the surgical brace device is configured to create a redundant line of joined tissue adjacent to the line of stapled tissue and to absorb energy associated with the tensile stress load during organ motion.

In a preferred embodiment of the present invention, a surgical brace device for deployment across a line of surgically stapled tissue of a bodily organ comprises a pair of splint members of a predetermined rigidity profile configured to be disposed on either side of the line of surgically stapled tissue; a strut member fixedly joined with the pair of splint members at one ends thereof; and a tie member configured to traverse tissue of the organ disposed at a predetermined distance from the strut member to interconnect the pair of splint members and anchor the surgical brace device to the organ. The pair of splint members is dimensioned to span the width of the line of stapled tissue and a predetermined portion of tissue of the organ adjacent thereto.

In an alternate embodiment of the present invention, a surgical brace device for deployment across a line of surgically stapled tissue of a bodily organ comprises: a pair of splint members configured to be disposed on either side of the surgically stapled tissue; a plurality of strut members fixedly joined with the pair of splint members at one ends thereof; and a plurality of tie members configured to traverse tissue of the organ disposed at a predetermined distance from the plurality of strut members to interconnect the pair of splint members and anchor the surgical brace device to the organ.

In an aspect of the present invention, the two opposing splint members interconnected by the tie member may be configured to apply a compression of predetermined magnitude to a portion of tissue of the organ adjacent to the line of stapled tissue and set back from the location of the tie member to cause permanent joining thereof and formation of a seal. In an alternate aspect the two opposing splint members may be configured to directly interact with a portion of tissue of the organ adjacent to the line of stapled tissue in such a way to absorb energy associated with dynamic tensile stress load thereon arising from physiological organ motion to reduce damaging effects thereof to the line of stapled tissue. In another alternate aspect, the two opposing splint members may be configured to cause permanent joining of tissue adjacent to the staple line to form a redundant seal line and to absorb energy of dynamic tensile stress load to protect the line of surgically stapled tissue from damaging effects thereof.

BRIEF DESCRIPTION OF THE DRAWINGS

The following exemplary figures are provided to supplement the description below and more clearly describe the invention. In the figures, like elements are generally designated with the same reference numeral for illustrative convenience and should not be used to limit the scope of the present invention.

DETAILED DESCRIPTION OF THE INVENTION

The novel features of the present invention will become apparent to those of skill in the art upon examination of the following detailed description of the invention. It should be understood, however, that the detailed description of the invention and the specific examples presented, while indicating certain embodiments of the present invention, are provided for illustration purposes only because various changes and modifications within the spirit and scope of the invention will become apparent to those of skill in the art from the detailed description of the invention and claims that follow.

Embodiments of the presently disclosed surgical instrument will now be described in detail with reference to the drawing figures wherein like reference numerals identify similar or identical elements. In the drawings and in the description which follows, the term "proximal", as is traditional, will refer to the end of the surgical instrument which is closest to the operator while the term "distal" will refer to the end of the device which is furthest from the operator.

Embodiments of the present invention relate to a surgical brace device for protecting a surgically stapled tissue of a bodily organ from failure caused by the technical limitations of the present surgical stapling technology and damaging effects of organ motion. Being configured to be disposed across a line of surgically stapled tissue of an organ the surgical brace device of the present invention aims to reduce probability of failure of the line of stapled tissue that may lead to morbidity or mortality brought on by deficiencies in the staple line due to the known technical limitations of the present surgical stapling technology and damaging effects of physiological organ motion. In various embodiments, the surgical brace device of the present invention is configured to create a redundant line of joined tissue on a portion of tissue of the organ adjacent to the line of stapled tissue and/or to provide energy absorbing barrier to the line of stapled tissue protecting it from damaging effects of the physiological organ motion.

Figure 1A:
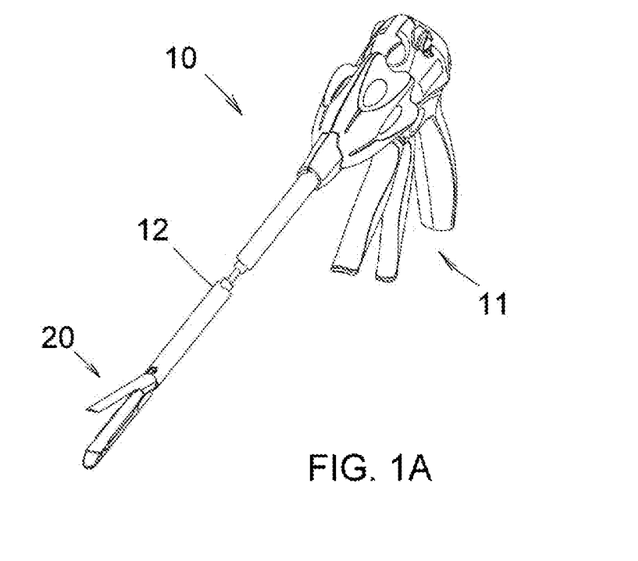
FIG. 1A is a perspective view of an exemplary surgical stapler instrument according to an embodiment of the present invention.
Figure 1B:
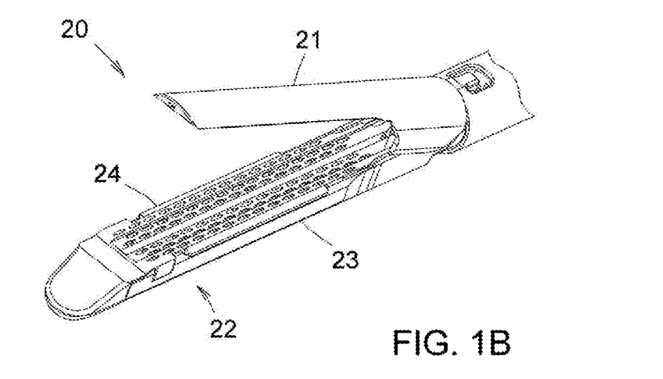
FIG. 1B is a perspective view of an exemplary end effector of a surgical stapler instrument according to an embodiment of the present invention.

Referring to FIGS. 1A and 1B, an exemplary prior art surgical stapler instrument 10 and an enlarged view of an end effector 20 thereof are shown. Surgical stapler instrument 10 includes a handle 11, an elongate end effector 20 and an elongate tube 12 that operatively connects handle 11 and end effector 20. End effector 20 comprises a first jaw member 21 and a second jaw member 22 extending from proximal to distal end defining a length thereof. Second jaw member 22 comprises an elongate channel or a cartridge bay 23 configured to releasably receive a staple cartridge 24 housing a plurality of staples and first jaw member 21 comprises an anvil that is aligned with and pivotally attached to cartridge bay 23 forming a pair of opposed jaw members that open and close, when operated on with handle 11 by the physician, to capture and compress a target tissue there-between for stapling. End effector 20 is configured in such a way that jaw members 21, 22 are capable of rigidly holding their approximated positional relationship when closed to compress the target tissue prior to and during the firing of staples.

Figure 2A:
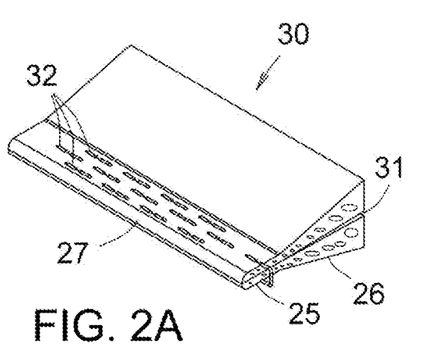
FIGS. 2A and 2B are schematic illustrations, in perspective and side elevation view, respectively, of a sectioned tissue of an organ cut and joined by a row of staples with the organ resting according to an embodiment of the present invention.
Figure 2B:
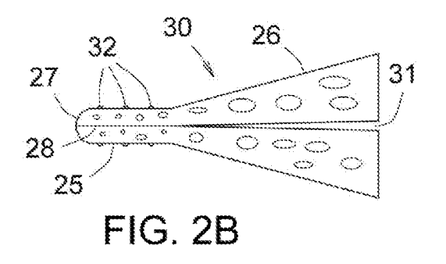
Figure 2C:
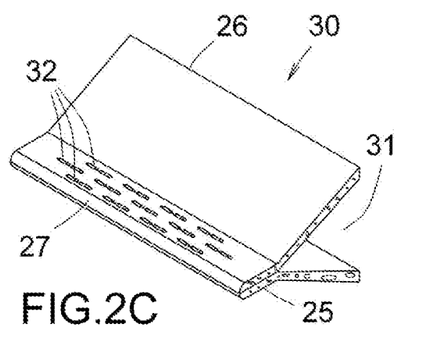
FIGS. 2C and 2D are schematic illustrations, in perspective and side elevation view, respectively, of a sectioned tissue of an organ cut and joined by a row of staples with the organ in motion according to an embodiment of the present invention.
Figure 2D:
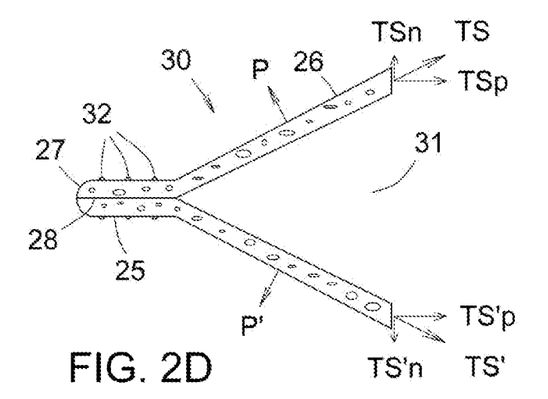

FIGS. 2A and 2B schematically show, in perspective and side elevation view, respectively, of a sectioned tissue 25, 26 comprising an organ 30, having a lumen 31, cut and joined by a plurality of rows of staples 32 forming a cut edge 27 and a line of stapled tissue 25, which may also be referred to as a stapled tissue, a surgically stapled tissue, a line of stapled tissue or a staple line, hereinafter, and tissue 26 adjacent thereto with tubular organ 30 resting between cycles of physiological motion, for example, breathing or digesting. FIGS. 2C and 2D schematically show, in perspective and side elevation view, respectively, tubular organ 30, shown in FIGS. 2A and 2B, in the middle of a cycle of physiological motion with directions of loads from internal luminal pressure, substantially perpendicular to the wall tissue of tubular organ 30, and directions of tensile stresses on the wall tissue represented by arrows indicated by P, P' and TS, TS', respectively, as shown in FIG. 2D.

As schematically illustrated in FIG. 2D with internal pressure built up in the lumen of tubular organ 30 during a physiological motion thereof, for example, an inhalation phase of a breathing cycle, a given area of the wall tissue of tubular organ 30 is subjected to an outward pressure load and a tensile stress load in directions substantially perpendicular and coplanar to the area, respectively. Whereas the magnitude of an outward pressure load on a given area of the wall tissue is largely determined by the internal lumen pressure, that of a tensile stress load at the same area is correlated with the loads from internal lumen pressure acting on the rest of area of the wall tissue of tubular organ 30 and thus, largely dependent on the size and shape of tubular organ 30 with sizable variation depending on location on the wall tissue thereof. For this reason tensile stress load on the wall tissue of tubular organ 30 generally is likely to have more significant impact on the integrity of a line of stapled tissue on tubular organ 30 than load from internal lumen pressure. For example, in the lung during a normal breathing cycle, the internal lumen pressure, more precisely, pressure differential across the wall tissue thereof, is only a very small fraction of an ambient atmospheric pressure and thus the pressure load on a given area cannot be large. On the contrary the magnitude of tensile stress load at an area on the wall tissue could be much larger than the pressure load due to the fact that internal lumen pressure load acting on substantially all of the rest of the wall tissue could contribute to creating the tensile stress load. During a cough, i.e., forced exhalation, the internal lumen pressure of the lung could reach a sizable fraction of an ambient atmospheric pressure and tensile stress load on the wall tissue of the lung could be even more substantial. It is to be noted in FIG. 2D that the components of tensile stress loads TS, TS', indicated as TSn, TS'n, substantially perpendicular to an interface 28 of stapled tissue (shown as a line intersecting the staples 32) are in opposite direction with each other while the components, indicated as TSp, TS'p, substantially parallel thereto are in the same direction towards lumen 31. The components TSn and TS'n act in such a way to pull apart line of stapled tissue 25 while combined action of the components of TSp and TS'p is to harmlessly pull line of stapled tissue 25 towards lumen 31 of tubular organ 30. It is also to be noted that the magnitudes of components TSn and TS'n are highly correlated with the opening angle between wall tissue 26 at the distal edge of stapled tissue 25 and therefore, one method to reduce damaging effects from these components of tensile stress load would be to keep the opening angle as small as possible, that is, to maintain wall tissue 26 as inline or coplanar with interface 28 as possible at least in the vicinity of line of stapled tissue 25.

Figure 3A:
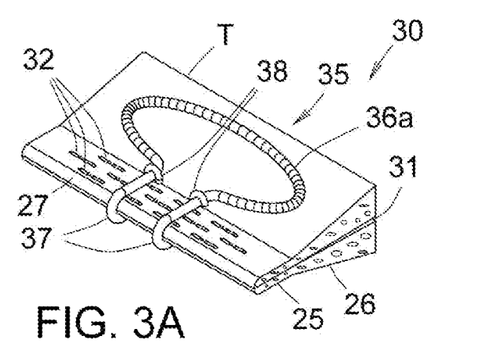
FIGS. 3A and 3B are schematic illustrations, in perspective and side elevation view, respectively, of a surgical brace device deployed on a sectioned tissue of an organ cut and joined by a row of staples with the organ resting according to an embodiment of the present invention.
Figure 3B:
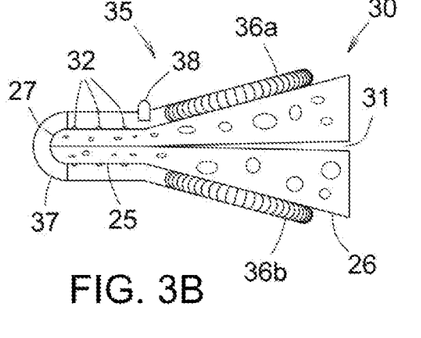
Figure 3C:
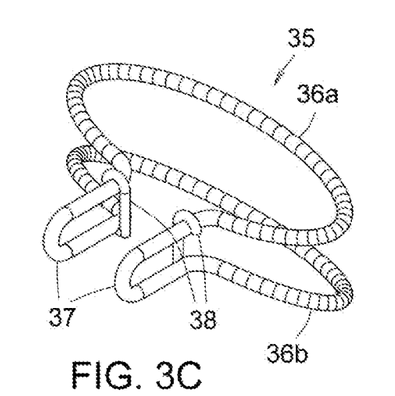
FIGS. 3C and 3D are schematic illustrations, in perspective and exploded view, respectively, of a surgical brace device according to an embodiment of the present invention.
Figure 3D:
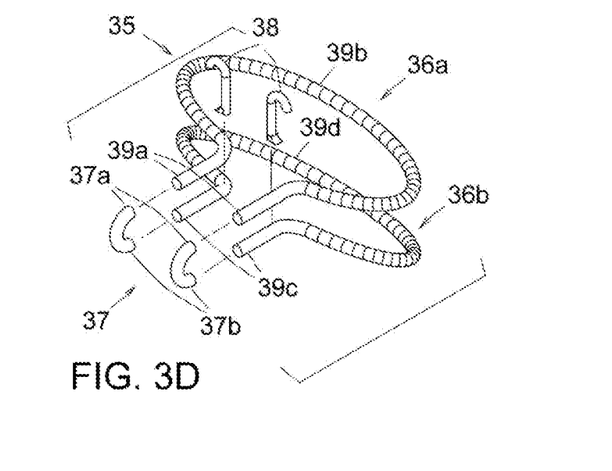

Referring to FIGS. 3A and 3B schematically showing, in perspective and side elevation view, respectively, a surgical brace device 35 deployed on a sectioned tissue 25, 26 of an organ 30 with a lumen 31 therein cut and joined by a plurality of rows of staples 32 with tubular organ 30 shown in a resting state between cycles of physiological motion, and to FIGS. 3C and 3D schematically showing surgical brace device 35, in perspective and exploded view, respectively, in a preferred embodiment of the present invention, surgical brace device 35 for deployment across a line of surgically stapled tissue of a bodily organ comprises: a first splint member and a second splint member 36a, 36b having a first end and a second end 39a, 39b, and 39c, 39d, respectively, configured to be disposed on either side of tissue 25, 26; a strut member 37 having a first end and a second end 37a, 37b, and disposed adjacent to cut edge 27 outwardly from line of stapled tissue 25, wherein a first end 37a of strut member 37 is fixedly joined with a first end 39a of a first splint member 36a cantilevering therefrom and a second end 37b of strut member 37 is fixedly joined with a first end 39c of a second splint member 36b cantilevering therefrom, and wherein a first splint member and a second splint member 36a, 36b are dimensioned to span the full width of line of stapled tissue 25 and a predetermined portion of tissue 26 adjacent thereto; and a tie member 38 configured to traverse tissue comprising tubular organ 30 to interconnect and keep a first splint member and a second splint member 36a, 36b from spreading apart, and disposed in tissue 26 past the last row of staples from cut edge 27 at a predetermined distance from strut member 37 anchoring surgical brace device 35 to tubular organ 30. In an alternate embodiment surgical brace device 35 may comprise a plurality of strut members. In another alternate embodiment surgical brace device 35 may comprise a plurality of tie members. In another alternate embodiment tie member 38 may be disposed embedded in stapled tissue 25. In another alternate embodiment strut member 37 may be disposed embedded in stapled tissue 25 and a first splint member and a second splint member 36a, 36b may be dimensioned to span at least a portion of the width of line of stapled tissue 25 and a predetermined portion of tissue 26 adjacent thereto.

In an alternate embodiment of the present invention, surgical brace device 35 for deployment across a line of surgically stapled tissue adjacent to tissue of an organ comprises: a wire form comprising a first splint member portion and a second splint member portion 36a, 36b, having predetermined shapes conforming to contours of predetermined surfaces and configured to be disposed on either side of line of surgically stapled tissue 25 and tissue 26 in opposite positional relation with each other; a strut member portion 37 disposed between a first splint member portion and a second splint member portion 36a, 36b cantilevering therefrom and adjacent to cut edge 27 outwardly from line of stapled tissue 25, wherein a first splint member portion and a second splint member portion 36a, 36b are dimensioned to span the full width of line of stapled tissue 25 and a predetermined portion of tissue 26 adjacent thereto; and a tie member 38 configured to traverse tissue comprising tubular organ 30 to interconnect and keep a first splint member portion and a second splint member portion 36a, 36b from spreading apart, and disposed in tissue 26 past the last row of staples from cut edge 27 at a predetermined distance from strut member portion 37 anchoring surgical brace device 35 to tubular organ 30. In another alternate embodiment, as will be further described in relation to FIG. 5E, a surgical brace device for deployment across a line of surgically stapled tissue adjacent to tissue of an organ comprises: a shaped plate comprising a first splint member portion and a second splint member portion having predetermined shapes conforming to contours of predetermined surfaces and configured to be disposed on either side of the line of the surgically stapled tissue and tissue in opposite positional relation with each other; a strut member portion disposed between a first splint member portion and a second splint member portion cantilevering therefrom and adjacent to the cut edge of the line of stapled tissue outwardly therefrom, wherein a first splint member portion and a second splint member portion are dimensioned to span the full width of the line of stapled tissue and a predetermined portion of the tissue adjacent thereto; and a tie member configured to traverse tissue comprising the organ to interconnect and keep a first splint member portion and a second splint member portion from spreading apart, and disposed in the tissue past the last row of staples from the cut edge at a predetermined distance from the strut member portion anchoring the surgical brace device to the organ.

Still referring to FIGS. 3A-3D, in a preferred embodiment of the present invention a first splint member and a second splint member 36a, 36b comprising surgical brace device 35 may comprise an elongate member shaped into predetermined configurations, divisible into two portions, for the sake of mechanical analysis, a proximal portion disposed proximally with respect to cut edge 27 of line of stapled tissue 25 between strut member 37 and tie member 38 and a distal portion disposed distally with respect to cut edge 27 past tie member 38. In an alternate embodiment splint members 36a, 36b may be constructed out of material other than an elongate shape as will be described in relation to FIG. 5E. In an embodiment the distal portions of splint members 36a, 36b may be configured substantially as a loop or a part thereof and the proximal portions may be configured to extend between the distal portions and strut member 37. In an alternate embodiment the distal portions may be of a shape other than a loop as will be described in relation to FIGS. 5E and 5G hereinafter. In an embodiment the proximal portions may be substantially of a linear configuration. In an alternate embodiment the proximal portions may be of a shaped configuration. In an embodiment splint member 36a, 36b are substantially of the same configuration. In an embodiment splint member 36a, 36b are substantially of dissimilar configurations.

Being disposed in close contact with and to span a portion of tissue 26 of tubular organ 30 the distal portions of splint members 36a, 36b interact with and oppose outward expansion with respect to lumen 31 of tissue 26 of tubular organ 30 during physiological motion thereof as will be further describe in relation to FIG. 3E in the following section. The proximal portions of splint members 36a, 36b transfer loads imparted on the distal portions by tissue 26 during physiological motion of tubular organ 30 to strut member 37. In an embodiment, splint members 36a, 36b may be configured in such a way and constructed out of material that may provide a predetermined rigidity profile and a predetermined resilience profile to the distal portions thereof substantially in the direction perpendicular to cut edge 27 and interface 28 of stapled tissue (as shown in FIG. 2B), and a predetermined rigidity to the proximal portions thereof. In an embodiment strut member 37 may be of an elongate configuration and constructed out of material that may provide a predetermined columnar strength sufficient to resist deformation under compressive loads from the distal portions of splint members 36a, 36b. In an embodiment, splint members 36a, 36b and strut member 37 may be constructed as a unit out of a single elongate member. In an alternate embodiment, splint members 36a, 36b and strut member 37 may be constructed out of separate material. Tie member 38 comprising surgical brace device 35 is subjected to a tensile stress load from the distal portions of splint members 36a, 36b opposing outward expansion of tissue 26. In an embodiment tie member 38 may be constructed out of material that may provide a predetermined tensile strength thereto to be able to sustain a tensile load from splint member 36a, 36b and configured to minimize tissue damage in traversing tissue of tubular organ during deployment of surgical brace device 35. In an embodiment tie member 38 may be made of material bendable or deformable to facilitate deployment of surgical brace device 35 using a dedicated applicator instrument. In an embodiment tie member 38 may be of an elongate configuration with one end fixedly attached to one of the splint members comprising the surgical brace device and the other end bent to engage the other splint member during deployment of the surgical brace device.

In a preferred embodiment, an elongate member comprising splint members 36a, 36b may be made of a metal alloy having a superelastic property. In an alternate embodiment the metal comprising the elongate member may be of an ordinary type of metal with high degree of elasticity. In an alternate embodiment the elongate member comprising splint members 36a, 36b may be constructed from a bio-compatible polymer including bio-absorbable polymer. In another alternate embodiment the elongate member may comprise a metal alloy coated with a biocompatible polymer. In an embodiment splint member 36a, 36b and strut member 37 may be constructed as a unitary body. In an alternate embodiment splint member 36a, 36b and strut member 37 may be constructed separately and fixedly joined thereafter.

Figure 3E:
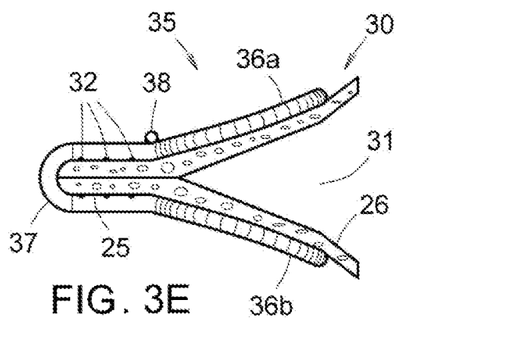
FIG. 3E is a schematic illustration, in side elevation view, of a surgical brace device, as shown in FIGS. 3A and 3B, with the organ in motion according to an embodiment of the present invention.

Referring to FIG. 3E showing, in side elevation view, a surgical brace device 35, as shown in FIGS. 3A and 3B, deployed on an organ 30 being shown in the middle of a cycle of physiological motion, in an embodiment of the present invention, surgical brace device 35 is configured to directly interacts with tissue 26 of tubular organ 30 adjacent to line of stapled tissue 25 to minimize damaging effects of tensile stress load thereon arising from physiological motion of tubular organ 30. In an embodiment the distal portions of splint members 36a, 36b that span a predetermined portion of tissue 26 are configured to deflect to a predetermined degree to absorb and store at least a portion of the energy associated with the tensile stress load present on tissue 26 as well as the loads from the internal pressure of lumen 31 of tubular organ 30. The deflection of splint members 36a, 36b helps prevent the tensile stress load from being concentrated on any one portion thereof, for example, at a second ends 39b, 39d. When properly configured for a particular application, splint members 36a, 36b effectively keeps the damaging components of loads acting on the wall tissue of tubular organ 30 from reaching line of stapled tissue 25 and tie member 38 traversing the wall tissue. By virtue of the geometry of surgical brace device 35 the forces of deflection of the distal portions of splint members 36a, 36b are transferred to strut member 37 through the proximal portions thereof and appear as a compressive load acting on opposite ends of strut member 37. Preferably, splint members 36a, 36b are configured to have such resilience characteristics to be able to return to the configuration as deployed at the end of each cycle of physiological motion of tubular organ 30.

Figure 4A:
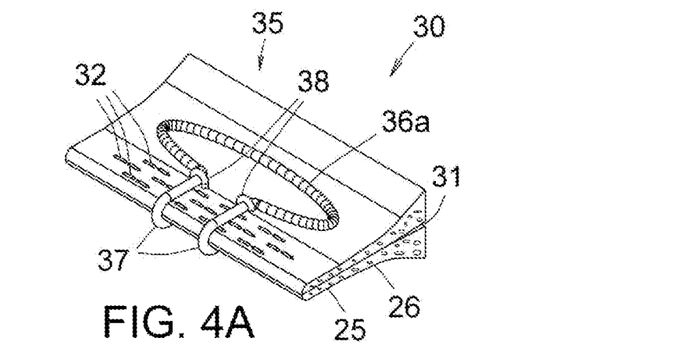
FIGS. 4A and 4B are schematic illustrations, in perspective and side elevation view, respectively, of a surgical brace device deployed on a sectioned tissue of an organ cut and joined by a row of staples with the organ resting according to an alternate embodiment of the present invention.
Figure 4B:
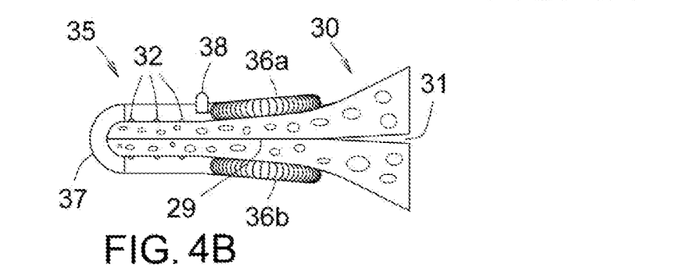
Figure 4C:
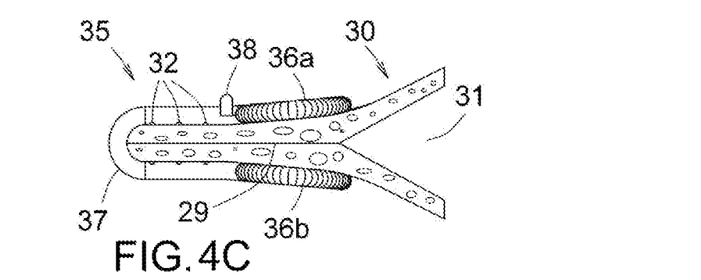
FIG. 4C is a schematic illustration, in side elevation view, of a surgical brace device, as shown in FIGS. 4A and 4B, with the organ in motion according to an alternate embodiment of the present invention.

Referring to FIGS. 4A and 4B schematically showing, in perspective and side elevation view, a surgical brace device 35 deployed on a sectioned tissue 25, 26 of an organ 30 shown in resting state and to FIG. 4C schematically showing, in side elevation view, surgical brace device 35 deployed on tubular organ 30 shown in the middle of physiological motion, in an alternate embodiment, surgical brace device 35 may be configured so that the distal portions of splint member 36a, 36b provide sufficient compression to a portion of tissue 26 to cause adhesion of tissue and create a region of permanently joined tissue 29 distally set back from line of stapled tissue and tie member 38. The region of joined tissue 29 may be considered an extension of line of stapled tissue 25 but without any penetrating wound from rows of staples 32 or tie member 38. As can be seen more clearly in FIG. 4C the region of newly joined tissue could not only act as a buffer to the loads present on the tissue of the organ effective blocking it from the line of stapled tissue and tie member but also as a secondary fluid-tight seal holding up integrity of the staple line even in the event a failure occurs at a portion of the line of stapled tissue. In an alternate embodiment, surgical brace device 35 may be configured so that the splint members cause to form a lined of joined tissue on a portion of the tissue of an organ and absorb at least a portion of energy associated with loads present thereon.

Figure 4D:
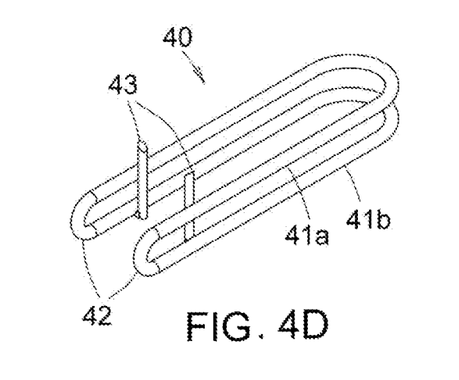
FIG. 4D is a schematic illustration, in perspective view, of a surgical brace device stowed in an end effector of a dedicated endoscopic applicator instrument according to an embodiment of the present invention.

Referring to FIG. 4D showing, in perspective view, of a surgical brace device 40 arranged for stowage in an end effector of an endoscopic instrument dedicated for application thereof across a line of stapled tissue, in a preferred embodiment of the present invention, at least a portion of splint members 41a, 41b comprising surgical brace device 40 may be made of a Ni—Ti alloy material exhibiting a superelastic property near body temperature so that splint members 41a, 41b may be able to spring back to the design configuration when released from the end effector during deployment of surgical brace device 40. This would allow a surgical brace device to be designed to have splint members with profiles larger than what the requirements for stowage in an end effector would dictate and in turn, help reduce the number of surgical brace devices required to cover a given length of a staple line than otherwise possible.

Figure 5A:
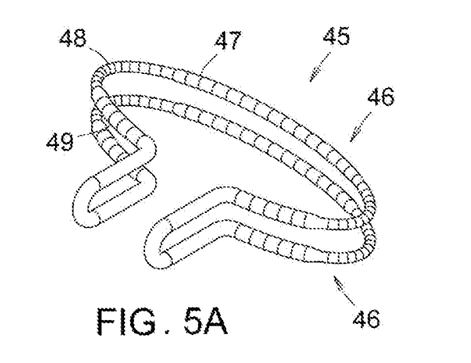
FIGS. 5A-5E are schematic illustrations, in perspective views, of splint members and a strut member comprising a surgical brace device according to various embodiments of the present invention.
Figure 5B:
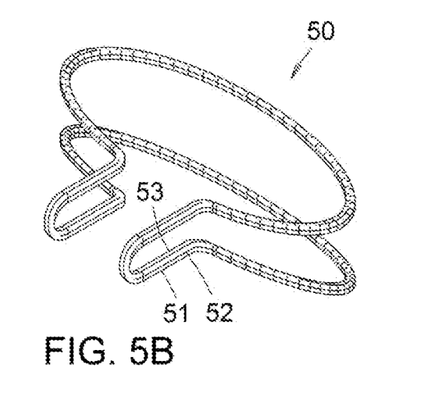
Figure 5C:
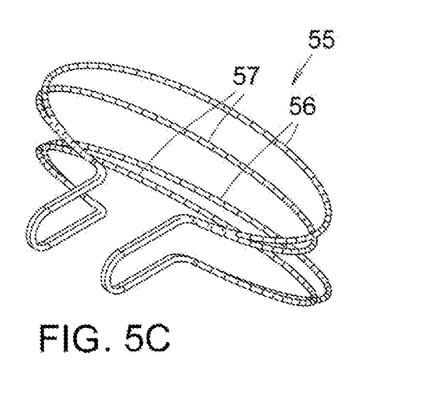

FIGS. 5A-5C show in perspective views the splint members and strut member comprising a surgical brace device in various embodiments of the present invention. In an embodiment, as shown in FIG. 5A, cross sectional dimension of an elongate member comprising splint members 46 comprising surgical brace device 45 may be varied along the length thereof to tune the rigidity and resilience profiles of splint members 46 to suit a particular application. In an alternate embodiment the cross sectional profile of elongate members 46 may be varied along the length thereof. For example, a metal wire comprising the elongate member may be of larger diameter at portions 47, 49 of loops comprising splint members 46 than that at portions 48 thereof. Being disposed substantially parallel to the line of stapled tissue portions 47, 49 largely act as load bearing members and portions 48, being substantially transverse thereto, act as a flexible member providing resilience characteristics to splint members 46. In an alternate embodiment, as schematically shown in FIG. 5B, the splint members comprising a surgical brace device 50 may comprise a plurality of elongate members 51, 52, 53 substantially of the same configuration bundled together. In another alternate embodiment a plurality of elongate members 51, 52, 53 may be braided to form the splint members. In another alternate embodiment, as schematically shown in FIG. 5C, the splint members comprising a surgical brace device 55 may comprise a plurality of elongate members 56, 57 substantially of different configurations. Constructing splint members out of multiple components may provide a freedom in optimizing the design of a surgical brace device for a particular application and may expand options for manufacturing of the purpose designed surgical brace device as well.

Figure 5D:
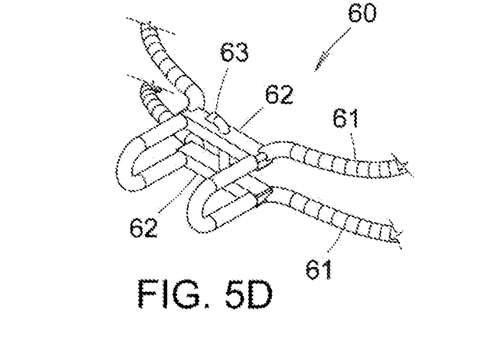
Figure 5E:
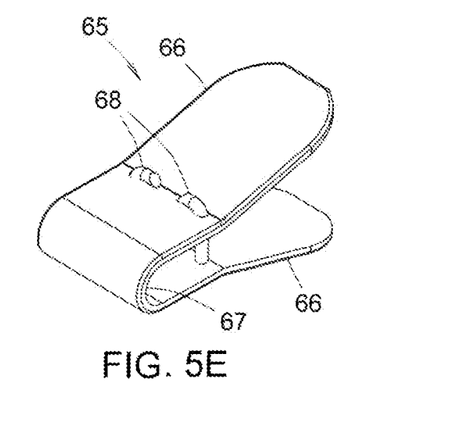
Figure 5F:
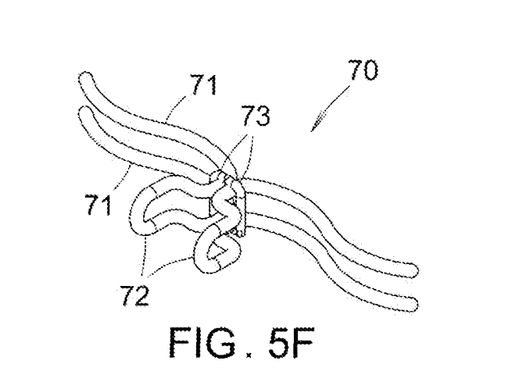
FIGS. 5F and 5G are schematic illustrations, in perspective view, of a surgical brace device as deployed and stowed in an end effector, respectively, according to various alternate embodiments of the present invention.
Figure 5G:
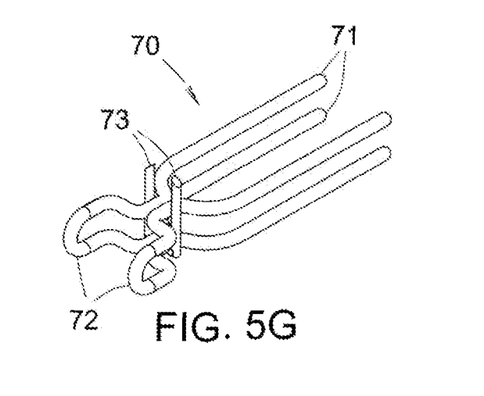

As shown in FIG. 5D a surgical brace device 60 may further comprise cross braces 62 disposed at a predetermined location thereon to enhance structural rigidity in an embodiment of the present invention. Cross braces may also provide structural elements with which tie members 63 may engage to interconnect splint members 61. Referring to FIG. 5E showing a surgical brace device in an alternate embodiment of the present invention, surgical brace device 65 may comprise a plate member of predetermined dimensions shaped to construct splint members 66 and strut member 67, and tie members 68. Referring to FIG. 5F, in an alternate embodiment of the present invention proximal and distal portions of splint members 71 comprising surgical brace device 70 may be of curved line configurations. Shown in FIG. 5G is a surgical brace device 70, as shown in FIG. 5F, stowed in an end effector of a dedicated applicator instrument prior to deployment, where splint members 71 are made of a superelastic metal wire.

Figure 6A:
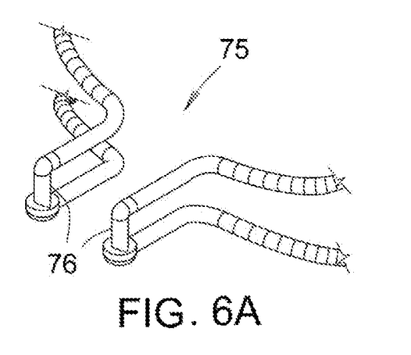
FIGS. 6A and 6B are schematic illustrations, in perspective view, of a strut member and splint members, partially broken away, comprising a surgical brace device according to various embodiments of the present invention.
Figure 6B:
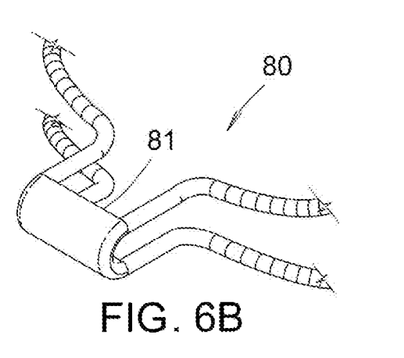
Figure 7A:
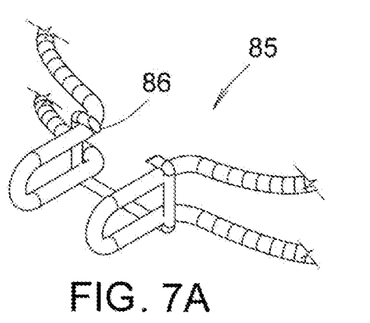
FIGS. 7A-7C are schematic illustrations, in perspective view, of a tie member comprising a surgical brace device according to various embodiments of the present invention.
Figure 7B:
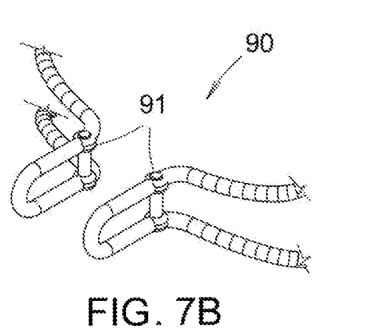
Figure 7C:
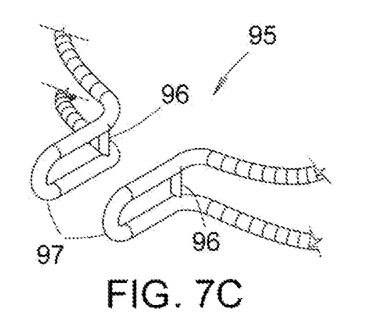

In an embodiment of the present invention, as shown in FIG. 6A, strut member 76 comprising a surgical brace device 75 may be configured to traverse the stapled tissue of an organ with minimal damage to tissue. Strut member 76 embedded in the stapled tissue may help prevent potential adverse interactions with neighboring bodily organs. In an alternate embodiment, as shown in FIG. 6B, strut member 81 comprising a surgical brace device 80 may further comprise a cross brace to enhance structural rigidity thereof. In an embodiment, as shown in FIG. 7A, tie members 86 comprising a surgical brace device 85 may comprise a staple the legs of which may be bent during deployment of surgical brace device 85 to interconnect the splint members. In an alternate embodiment, as shown in FIG. 7B, tie members 91 comprising a surgical brace device 90 may comprise deformable members that may be crimped to interconnect the splint members. In another alternate embodiment, as shown in FIG. 7C, tie members 96 comprising a surgical brace device 95 may be configured to traverse and be embedded in tissue of an organ with one end fixedly joined with a splint member to anchor surgical brace device 95 to the organ. In this case strut member 97 may be configured to have sufficient rigidity to be able to oppose the loads transferred thereto from the splint members to prevent deformation of surgical brace device 95.

While preferred illustrative embodiments of the invention are described above, it will be apparent to those skilled in the art that various changes and modifications may be made therein without departing from the invention. Accordingly, the appended claims should be used to interpret the scope of the present invention.

What is claimed is:

1. A surgical brace device for deployment across a line of stapled tissue of a bodily organ surgically stapled and cut forming a cut edge and having tissue adjacent to said line of stapled tissue opposite said cut edge comprising:

a first structural member and a second structural member, each comprising a proximal portion and a distal portion, said distal portion having a predetermined rigidity profile and a predetermined resilience profile substantially in the direction perpendicular to said line of stapled tissue, and each having a first end and a second end;

a first interconnect member fixedly joined with said first ends of said first structural member and said second structural member cantilevering therefrom; and a second interconnect member configured to traverse the tissue of said bodily organ, and interconnect said first structural member and said second structural member at a predetermined distance from said first interconnect member anchoring said surgical brace device to said bodily organ;

wherein said first structural member and said second structural member is configured to be disposed on either side of said line of stapled tissue and to apply a compression of predetermined magnitude to said tissue adjacent to said line of stapled tissue;

wherein said proximal portion of said first structural member and said second structural member is dimensioned to span at least a predetermined portion of the width of said line of stapled tissue, and said distal portion of said first structural member and said second structural member is dimensioned to span a predetermined portion of said tissue adjacent to said line of stapled tissue; and wherein said rigidity profile and resilience profile of said distal portion of said first structural member and said second structural member is predetermined to provide sufficient compression to a portion of said tissue to cause adhesion of tissue and create a region of permanently joined tissue distally set back from said line of stapled tissue and said second interconnect member.

2. A surgical brace device for deployment across a line of stapled tissue of a bodily organ surgically stapled and cut forming a cut edge and having tissue adjacent to said line of stapled tissue opposite said cut edge comprising:

a first structural member and a second structural member, each comprising a proximal portion and a distal portion, and each having a first end and a second end;

a first interconnect member fixedly joined with said first ends of said first structural member and said second structural member cantilevering therefrom; and a second interconnect member configured to traverse the tissue of said bodily organ, and interconnect said first structural member and said second structural member at a predetermined distance from said first interconnect member anchoring said surgical brace device to said bodily organ;

wherein said first structural member and said second structural member is configured to be disposed on either side of said line of stapled tissue and to apply a compression of predetermined magnitude to said tissue adjacent to said line of stapled tissue;

wherein said proximal portion of said first structural member and said second structural member is dimensioned to span at least a predetermined portion of the width of said line of stapled tissue, and said distal portion of said first structural member and said second structural member is dimensioned to span a predetermined portion of said tissue adjacent to said line of stapled tissue; and wherein said first structural member and said second structural member is substantially of the same configuration.

3. A surgical brace device for deployment across a line of stapled tissue of a bodily organ surgically stapled and cut forming a cut edge and having tissue adjacent to said line of stapled tissue opposite said cut edge comprising:

a first structural member and a second structural member, each comprising a proximal portion and a distal portion, and each having a first end and a second end;

a first interconnect member fixedly joined with said first ends of said first structural member and said second structural member cantilevering therefrom; and a second interconnect member configured to traverse the tissue of said bodily organ, and interconnect said first structural member and said second structural member at a predetermined distance from said first interconnect member anchoring said surgical brace device to said bodily organ;

wherein said first structural member and said second structural member is configured to be disposed on either side of said line of stapled tissue and to apply a compression of predetermined magnitude to said tissue adjacent to said line of stapled tissue;

wherein said proximal portion of said first structural member and said second structural member is dimensioned to span at least a predetermined portion of the width of said line of stapled tissue, and said distal portion of said first structural member and said second structural member is dimensioned to span a predetermined portion of said tissue adjacent to said line of stapled tissue; and wherein said first structural member and said second structural member, and said first interconnect member is constructed as a unitary body.

* * * * *